(12) United States Patent
Watanabe et al.

(10) Patent No.: US 9,933,410 B2
(45) Date of Patent: *Apr. 3, 2018

(54) BIOLOGICAL SAMPLE MEASUREMENT DEVICE

(71) Applicant: Panasonic Healthcare Holdings Co., Ltd., Minato-ku, Tokyo (JP)

(72) Inventors: Takahiro Watanabe, Ehime (JP); Masumi Aono, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/453,917

(22) Filed: Mar. 9, 2017

(65) Prior Publication Data

US 2017/0176409 A1 Jun. 22, 2017

Related U.S. Application Data

(63) Continuation of application No. 13/985,734, filed as application No. PCT/JP2012/002016 on Mar. 23, 2012, now Pat. No. 9,625,441.

(30) Foreign Application Priority Data

Mar. 31, 2011 (JP) .................................. 2011-077625
Nov. 24, 2011 (JP) .................................. 2011-256236

(51) Int. Cl.
*G01N 33/487* (2006.01)
*G06F 19/00* (2018.01)
(Continued)

(52) U.S. Cl.
CPC ... *G01N 33/48792* (2013.01); *G06F 19/3418* (2013.01); *A61B 5/157* (2013.01); *A61B 5/150022* (2013.01); *G01N 33/44* (2013.01)

(58) Field of Classification Search
CPC ........ A61B 2560/0242; A61B 2562/08; A61B 5/1411; A61B 5/14532; A61B 5/157;
(Continued)

(56) References Cited

U.S. PATENT DOCUMENTS 6,529,446 B1 3/2003 de la Huerga
8,992,834 B2 3/2015 Nomura et al.
(Continued)

FOREIGN PATENT DOCUMENTS

EP 2333551 A1 6/2011
JP 2005-121558 A 5/2005
(Continued)

OTHER PUBLICATIONS

Search Report from the corresponding International Patent Application No. PCT/JP2012/002016 dated May 15, 2012.
(Continued)

*Primary Examiner* — Randy Gibson
*Assistant Examiner* — Gedeon M Kidanu
(74) *Attorney, Agent, or Firm* — Shinjyu Global IP (57) ABSTRACT

A biological sample measurement device includes a biological sample measuring instrument and measurement-related information supply instrument which supplies measurement-related information. Measurement-related information supply instrument has reading unit which reads the measurement-related information, first storage unit which stores identification information of measurement-related information supply instrument, and transmission unit which transmits the measurement-related information and the identification information of measurement-related information supply instrument to the biological sample measuring instrument. The biological sample measuring instrument has a main body case which has a mounting portion of a biological sample detection sensor and a display unit, a measurement
(Continued)

unit which is connected to the mounting portion inside the main body case, a control unit which is connected to the measurement unit, and a reception unit which is connected to the control unit and receives the measurement-related information and the identification information of the measurement-related information supply instrument transmitted from the transmission unit.

6 Claims, 8 Drawing Sheets (51) Int. Cl.
*G01N 33/44* (2006.01)
*A61B 5/15* (2006.01)
*A61B 5/157* (2006.01)

(58) Field of Classification Search
CPC ......... C12Q 1/006; G01N 2035/00881; G01N 33/48792; G01N 35/00871; G06F 19/3406; G06F 19/3418
See application file for complete search history.

(56) References Cited

U.S. PATENT DOCUMENTS

| | | |
|---|---|---|
| 2002/0170823 A1 | 11/2002 | Housefield et al. |
| 2003/0052787 A1* | 3/2003 | Zerhusen ............ A47B 23/046 340/573.1 |
| 2003/0140928 A1 | 7/2003 | Bui et al. |
| 2004/0200480 A1 | 10/2004 | Faries, Jr. et al. |
| 2006/0145817 A1 | 7/2006 | Aikawa et al. |
| 2006/0194324 A1 | 8/2006 | Faries, Jr. et al. |
| 2006/0229502 A1 | 10/2006 | Pollock et al. |
| 2006/0259676 A1 | 11/2006 | Oberding et al. |
| 2007/0025877 A1 | 2/2007 | Hansen |
| 2007/0255756 A1 | 11/2007 | Satomura et al. |
| 2007/0267475 A1* | 11/2007 | Hoglund ............... G06F 19/327 235/375 |
| 2008/0004908 A1* | 1/2008 | Oh ....................... G06F 19/327 705/2 |
| 2008/0094215 A1* | 4/2008 | Amador ............. G06K 7/10366 340/572.1 |
| 2008/0161656 A1 | 7/2008 | Bruce et al. |
| 2008/0294024 A1 | 11/2008 | Cosentino et al. |
| 2009/0112333 A1* | 4/2009 | Sahai ..................... A61M 5/142 700/3 |
| 2009/0295541 A1* | 12/2009 | Roof .................. G06F 19/3462 340/10.1 |
| 2010/0001838 A1* | 1/2010 | Miodownik .......... G06F 19/327 340/10.1 |
| 2010/0036676 A1* | 2/2010 | Safdi ..................... G06F 19/321 705/2 |
| 2010/0123547 A1 | 5/2010 | Stevenson et al. |
| 2010/0253941 A1 | 10/2010 | Brady et al. |
| 2010/0256473 A1 | 10/2010 | Asama et al. |
| 2010/0256990 A1 | 10/2010 | Horiguchi et al. |
| 2010/0268052 A1 | 10/2010 | Asama et al. |
| 2010/0305421 A1 | 12/2010 | Ow-Wing |
| 2011/0112384 A1* | 5/2011 | Eisenhardt ........... A61B 5/0002 600/309 |
| 2011/0124996 A1 | 5/2011 | Reinke et al. |
| 2011/0196218 A1 | 8/2011 | Nomura et al. |
| 2013/0109417 A1 | 5/2013 | Nawy et al. |
| 2013/0124227 A1 | 5/2013 | Ellis |
| 2013/0184548 A1* | 7/2013 | Matsumura ...... G01N 35/00663 600/365 |
| 2013/0197843 A1* | 8/2013 | Matsumura .......... A61B 5/1411 702/85 |

FOREIGN PATENT DOCUMENTS

| | | |
|---|---|---|
| JP | 2005-147732 A | 6/2005 |
| JP | 2008-051357 A | 3/2008 |
| JP | 2010-085258 A | 4/2010 |
| JP | 2011-053229 A | 3/2011 |
| WO | WO2005000114 A2 | 1/2005 |
| WO | WO2012108935 A1 | 8/2012 |

OTHER PUBLICATIONS

Office Action from the co-pending U.S. Appl. No. 13/985,734 dated Aug. 26, 2015.
Office Action from the co-pending U.S. Appl. No. 13/985,734 dated Jan. 14, 2016.
Office Action from the co-pending U.S. Appl. No. 13/985,734 dated Jun. 17, 2016.
Notice of Allowance from the co-pending U.S. Appl. No. 13/985,734 dated Dec. 20, 2016.

* cited by examiner

BIOLOGICAL SAMPLE MEASUREMENT DEVICE

CROSS-REFERENCE TO RELATED APPLICATIONS

This application is a continuation application of and claims priority to U.S. application Ser. No. 13/985,734 filed on Aug. 15, 2013, which is a National Stage Application under 35 U.S.C. § 365 of International Application PCT/JP2012/002016, with an international filing date of Mar. 23, 2012, which claims priority to Japanese Patent Application No. 2011-256236 filed on Nov. 24, 2011, and Japanese Patent Application No. 2011-077625 filed on Mar. 31, 2011. The entire disclosures of U.S. application Ser. No. 13/985,734, International Application PCT/JP2012/002016, Japanese Patent Application No. 2011-256236, and Japanese Patent Application No. 2011-077625 are hereby incorporated herein by reference.

TECHNICAL FIELD

The present invention relates to a biological sample measurement device which includes a biological sample measuring instrument and a measurement-related information supply instrument supplying measurement-related information to the biological sample measuring instrument.

BACKGROUND ART

First, a biological sample measuring instrument of the related art will be described. The biological sample measuring instrument of the related art includes a main body case which has a mounting portion of a biological sample sensor and a display unit, a measurement unit which is arranged inside the main body case and connected to the mounting portion, a control unit which is connected to the measurement unit, and a measurement-related information reading unit (for example, a barcode scanner) which is connected to the control unit (for example, see PTL 1).

This biological sample measuring instrument is widely utilized at a hospital. At the hospital, in order to keep a measurement record, for example, measurement-related information, such as a measurer ID (individual identification information, and hereinafter, referred to as ID), a patient ID, and a biological sample sensor ID, is read using a barcode scanner of a biological sample measuring instrument. Thereafter, a measurement of a biological sample is performed, and the result is displayed on a display unit.

However, in the biological sample measuring instrument of the related art, the barcode scanner which reads the measurement-related information is arranged in the biological sample measuring instrument. Accordingly, when reading the measurer ID, the patient ID, and the biological sample sensor ID, it is necessary to read the measurement-related information with a heavy biological sample measuring instrument main body having the barcode scanner and the display unit. Hence, in a hospital service in which a measurement should be successively performed on a plurality of patients, the burden on the measurer is great.

CITATION LIST

Patent Literature

PTL 1: Pamphlet of International Publication No. WO2005/000114

SUMMARY OF THE INVENTION

The invention has been accomplished in consideration of the above-described problem, and an object of the invention is to provide a biological sample measurement device capable of reducing burden on a measurer.

A biological sample measurement device of the invention includes a biological sample measuring instrument, and a measurement-related information supply instrument which supplies measurement-related information to the biological sample measuring instrument. The measurement-related information supply instrument has a reading unit which reads the measurement-related information, a first storage unit which stores identification information of the measurement-related information supply instrument, and a transmission unit which transmits the measurement-related information and the identification information of the measurement-related information supply instrument to the biological sample measuring instrument. The biological sample measuring instrument has a main body case which has a mounting portion of a biological sample detection sensor and a display unit, a measurement unit which is connected to the mounting portion inside the main body case, a control unit which is connected to the measurement unit, and a reception unit which is connected to the control unit and receives the measurement-related information and the identification information of the measurement-related information supply instrument transmitted from the transmission unit of the measurement-related information supply unit.

With this configuration, the reading unit of the measurement-related information can be arranged in the measurement-related information supply instrument provided separately from the biological sample measuring instrument. Accordingly, the measurer can read the measurement-related information using the measurement-related information supply instrument, and can transmit the read measurement-related information with the identification information of the measurement-related information supply instrument to the biological sample measuring instrument. Therefore, the measurer does not need to read various kinds of measurement-related information with a heavy biological sample measuring instrument main body having the barcode scanner, the display unit, or the like, and as a result, it is possible to reduce the burden on the measurer.

DESCRIPTION OF EMBODIMENTS

Hereinafter, an embodiment of the invention will be described referring to the drawings. It should be noted that the invention is not limited to the following embodiment.

Figure 1:
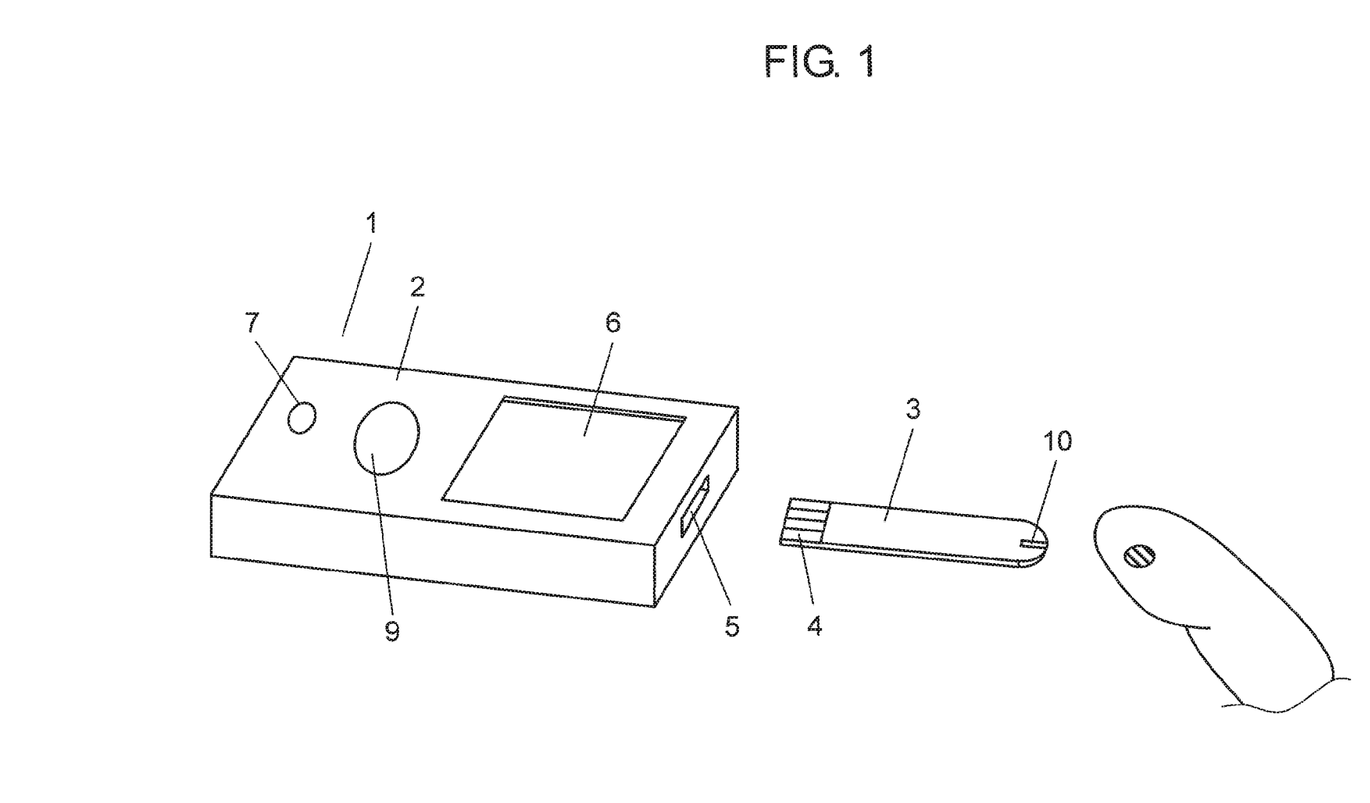
FIG. 1 is a perspective view of a biological sample measuring instrument which constitutes a biological sample measurement device according to an embodiment of the invention.

FIG. 1 is a perspective view of biological sample measuring instrument 1 which constitutes a biological sample measurement device according to an embodiment of the invention.

As shown in FIG. 1, biological sample measuring instrument 1 in the embodiment of the invention is, for example, a measuring instrument of a blood glucose level which is used at a hospital or the like. Biological sample measuring instrument 1 includes main body case 2 which is substantially formed in a rectangular shape. At the leading end of main body case 2, sensor mounting portion 5 into which connection terminal 4 of blood glucose level sensor (an example of a biological sample detection sensor) 3 is inserted is provided. In the surface of main body case 2, display unit 6, power switch 7, and reception unit 9 which receives measurement-related information from measurement-related information supply instrument 8 (see FIG. 2) are provided. Reception unit 9 is a reader which reads radio frequency identification (RFID) information, and performs RFID communication by electric waves. That is, in this embodiment, proximity communication by RFID communication is performed.

The measurer mounts connection terminal 4 of the blood glucose level sensor 3 in sensor mounting portion 5, and in this states, spots blood in spotting portion 10 at the leading end of blood glucose level sensor 3. Accordingly, the blood glucose level at this time is measured by measurement unit 11 (see FIG. 3) and displayed on display unit 6.

Biological sample measuring instrument 1 is placed on a wagon or the like and moved, for example, when moving between patient's rooms at a hospital, or the like.

Figure 2:
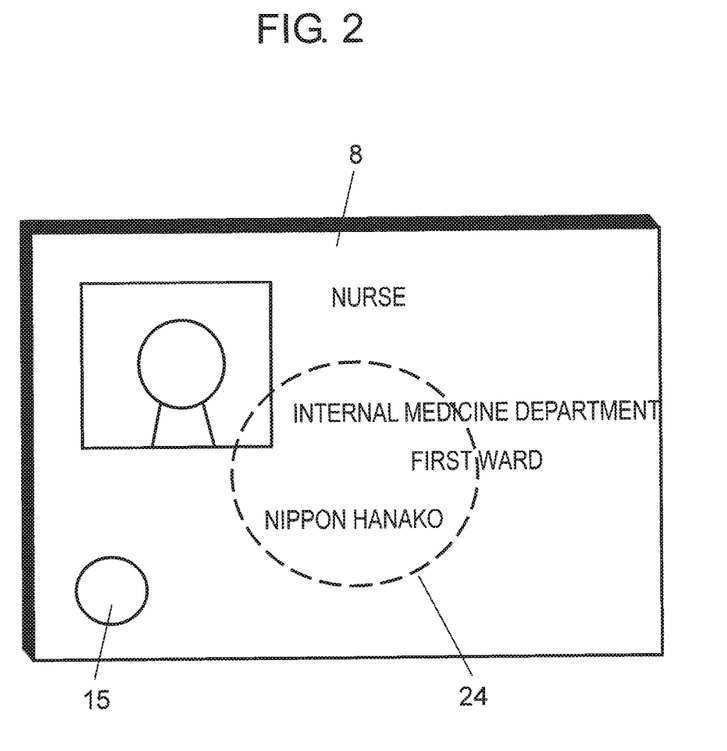
FIG. 2 is a perspective view of a measurement-related information supply instrument which constitutes a biological sample measurement device according to an embodiment of the invention.

FIG. 2 is a perspective view of measurement-related information supply instrument 8 constituting the biological sample measurement device according to the embodiment of the invention. Measurement-related information supply instrument 8 has a thin plate-shaped surface, and has a square card shape (square thin plate shape). Since single measurement-related information supply instrument 8 is supplied to each measurer (for example, a nurse) of a hospital, information of the measurer, for example, "NURSE, FIRST WARD OF INTERNAL MEDICINE DEPARTMENT, NIPPON HANAKO" is printed on the surface thereof.

Near the outer edge portion of the surface of measurement-related information supply instrument 8, in the example of FIG. 2, in a lower left portion, power switch 15 which is used to supply power to measurement-related information supply instrument 8 is provided. If power switch 15 is pressed, reading of measurement-related information or transmission of the read measurement-related information to biological sample measuring instrument 1 is performed. Reading and transmission are performed through proximity communication by RFID communication.

In this embodiment, the biological sample measurement device is constituted by a combination of single biological sample measuring instrument 1 and a plurality of measurement-related information supply instruments 8. However, the number of respective instruments constituting the biological sample measurement device is not limited to this example.

Figure 3:
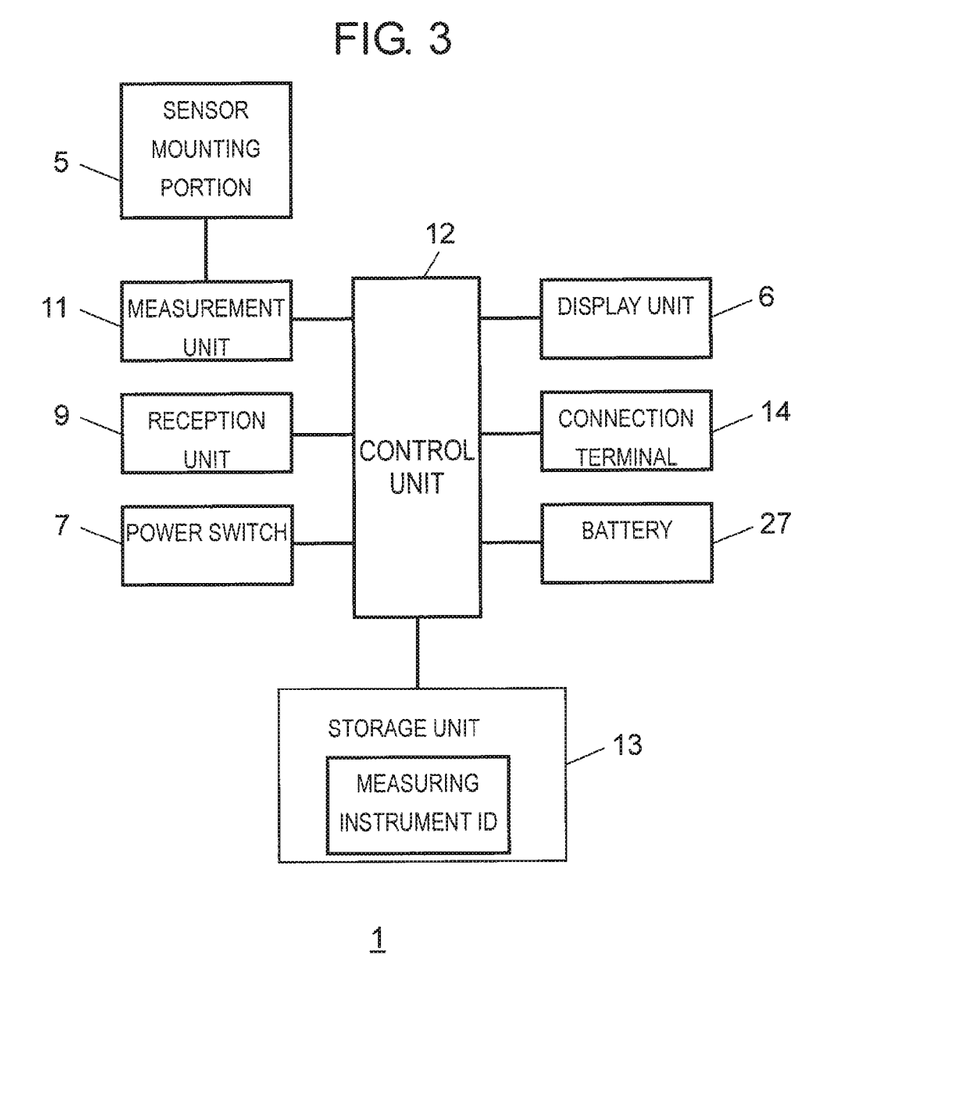
FIG. 3 is a control block diagram of a biological sample measuring instrument in an embodiment of the invention.

FIG. 3 is a control block diagram of biological sample measuring instrument 1 in the embodiment of the invention. Measurement unit 11 to which sensor mounting portion 5 is connected is connected to control unit 12. Reception unit 9 which receives measurement-related information by electric waves, power switch 7, display unit 6, and rechargeable battery 27 are connected to control unit 12. Storage unit 13 (second storage unit) is also connected to control unit 12, and authentication information (measuring instrument ID) of biological sample measuring instrument 1 is stored in storage unit 13.

Storage unit 13 stores measurement-related information received from measurement-related information supply instrument 8 through reception unit 9 under the control of control unit 12. Connection terminal 14 which provides measurement-related information stored in storage unit 13 to an external device is also connected to control unit 12.

Figure 4:
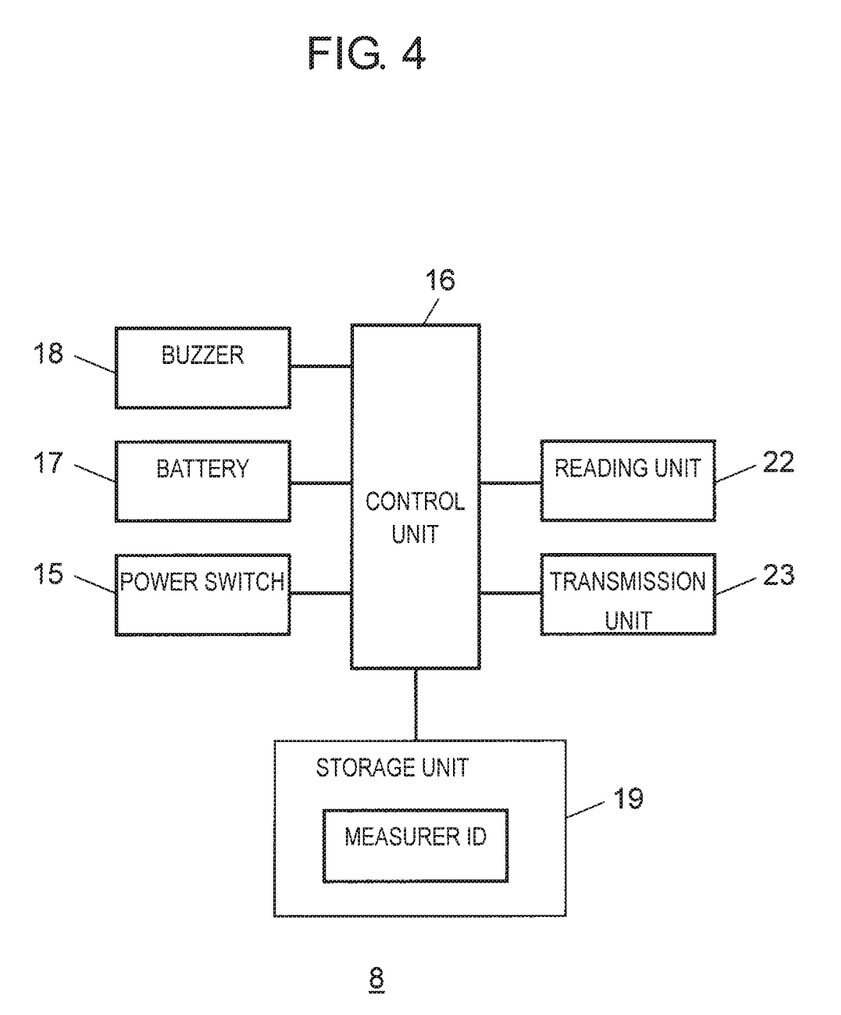
FIG. 4 is a control block diagram of a measurement-related information supply instrument in an embodiment of the invention.

FIG. 4 is a control block diagram of measurement-related information supply instrument 8 in the embodiment of the invention. Power switch 15 is connected to control unit 16. Battery 17, buzzer 18, and storage unit 19 (first storage unit) are connected to control unit 16. Authentication information (measurer ID) of measurement-related information supply instrument 8 is stored in storage unit 19.

Figure 5:
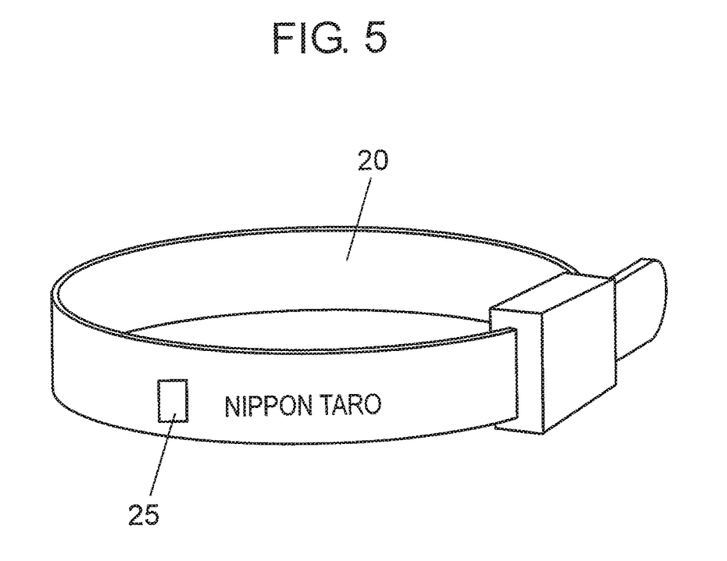
FIG. 5 is a perspective view of a bracelet which retains measurement-related information to be read by a measurement-related information supply instrument in an embodiment of the invention.
Figure 6:
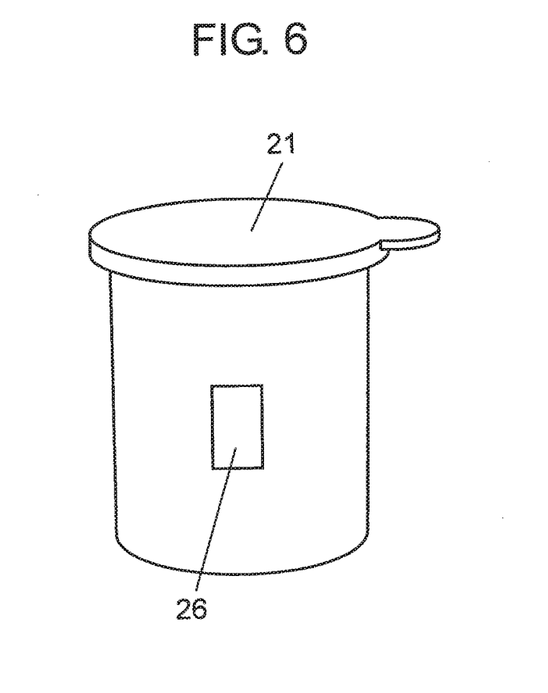
FIG. 6 is a perspective view of a blood glucose level sensor bottle which retains measurement-related information to be read by a measurement-related information supply instrument in an embodiment of the invention.

FIG. 5 is a perspective view of bracelet 20 which retains measurement-related information to be read by measurement-related information supply instrument 8 in the embodiment of the invention. FIG. 6 is a perspective view of blood glucose level sensor bottle 21 which holds measurement-related information to be read by measurement-related information supply instrument 8.

Reading unit 22 and transmission unit 23 which transmits measurement-related information read by reading unit 22 to reception unit 9 of biological sample measuring instrument 1 are connected to control unit 16. Reading unit 22 reads measurement-related information from bracelet 20 (see FIG. 5) of a patient or sensor bottle 21 (see FIG. 6) which accommodates blood glucose level sensor 3.

Reading unit 22 of measurement-related information supply instrument 8 is a reader which reads RFID information, and transmission unit 23 is constituted by a writer which transmits RFID information. As shown in FIG. 2, in the central portion of the surface of measurement-related information supply instrument 8, reading unit 22, transmission unit 23, and transmission/reception area 24 thereof are provided.

The RFID processing which is performed by reading unit 22 and transmission unit 23 is widely known, and thus detailed description thereof will be omitted. If transmission/reception area 24 of measurement-related information supply instrument 8 is held over (becomes close to) IC tag 25 incorporated in bracelet 20 (see FIG. 5) put on the patient, the patient ID in IC tag 25 is authenticated and read by reading unit 22.

Similarly, if transmission/reception area 24 of measurement-related information supply instrument 8 is held over (becomes close to) IC tag 26 incorporated in sensor bottle 21

(see FIG. 6), the biological sample sensor ID in IC tag 26 is authenticated and read by reading unit 22.

The operation of the biological sample measurement device described above will be described as to a case of being used at a hospital as an example.

Figure 7:
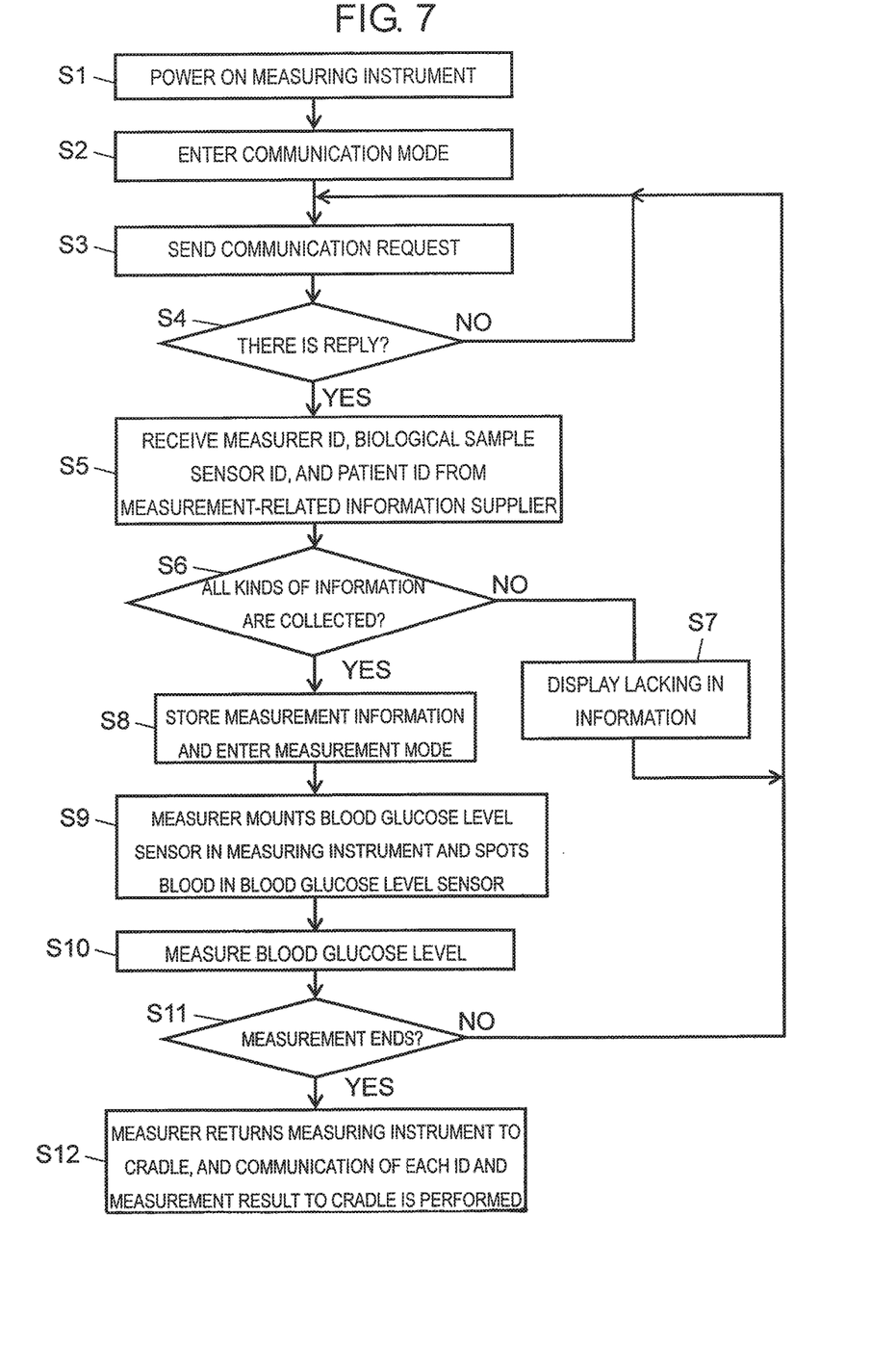
FIG. 7 is a flowchart showing a control flow of a biological sample measuring instrument in an embodiment of the invention.
Figure 8:
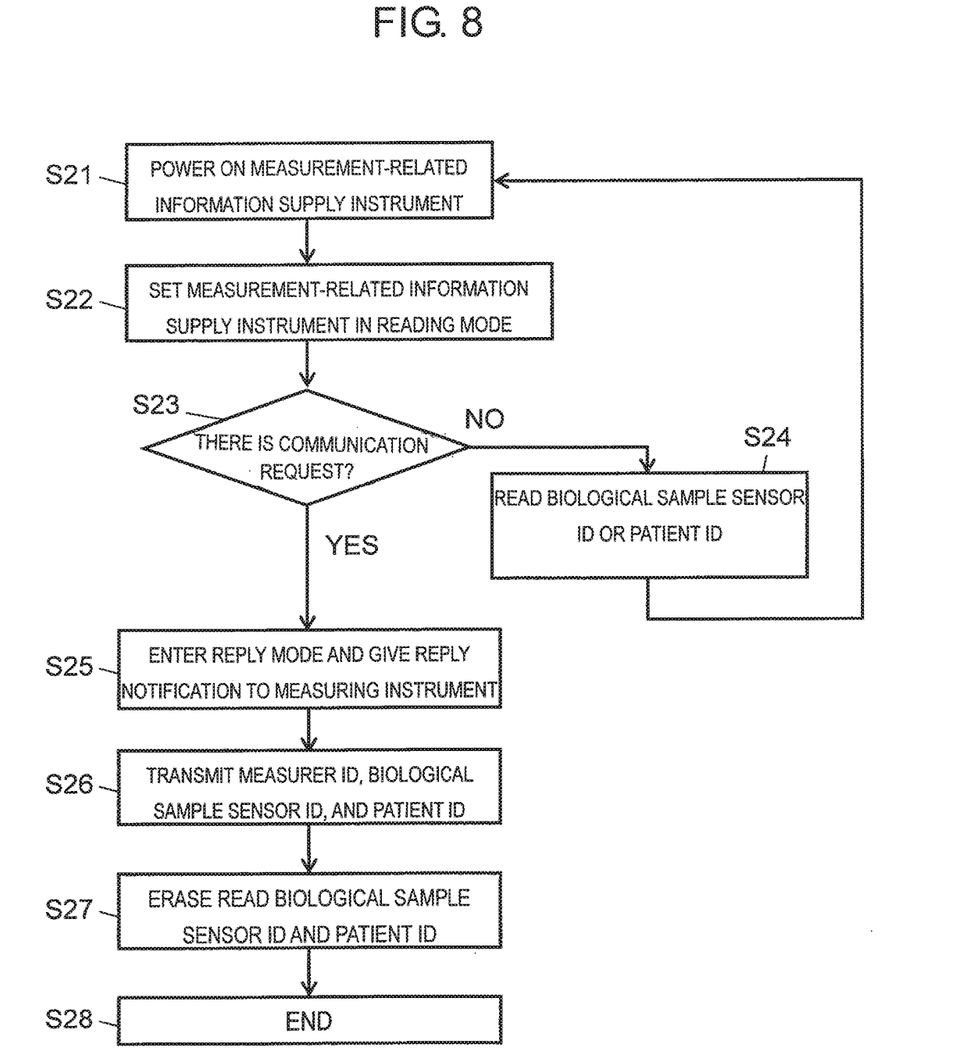
FIG. 8 is a flowchart showing a control flow of a measurement-related information supply instrument in an embodiment of the invention.

FIG. 7 is a flowchart showing a control flow of biological sample measuring instrument 1 in the embodiment of the invention. FIG. 8 is a flowchart showing a control flow of measurement-related information supply instrument 8 in the embodiment of the invention.

At the hospital, the measurer detaches biological sample measuring instrument 1 from a charging cradle (not shown). The measurer puts sensor bottle 21 (see FIG. 6) with biological sample measuring instrument 1 and blood glucose level sensor 3 accommodated therein on a wagon and carries the wagon into a patient's room.

At the hospital, in order to keep a measurement record, for example, there is a case where measurement-related information, such as a patient ID and a biological sample sensor ID, is collected for each measurement.

The measurer turns "on" power switch 7 of biological sample measuring instrument 1 to turn on biological sample measuring instrument 1. When this happens, power of battery 27 is supplied to control unit 12 of biological sample measuring instrument 1 (S1). Control unit 12 enters a communication mode (S2), sends a communication request to measurement-related information supply instrument 8 at a given interval using reception unit 9 (S3), and waits for a reply from measurement-related information supply instrument 8 (S4).

At this time, it is assumed that the measurer puts measurement-related information supply instrument 8 having a thin plate square card shape shown in FIG. 2 on his/her chest using a case made of, for example, transparent resin.

Here, the operation of measurement-related information supply instrument 8 corresponding to the operation of biological sample measuring instrument 1 described above will be described referring to FIG. 8.

The measurer detaches measurement-related information supply instrument 8 from the chest and presses power switch 15 of measurement-related information supply instrument 8. Then, power of battery 17 is supplied to measurement-related information supply instrument 8 (S21). Control unit 16 of measurement-related information supply instrument 8 enters a reading mode (S22). Control unit 16 confirms the presence/absence of a communication request to be sent from biological sample measuring instrument 1 in Step S3 (FIG. 7) using reading unit 22 (S23).

When there is no communication request from biological sample measuring instrument 1, that is, when the measurer does not hold (does not put) measurement-related information supply instrument 8 over (close to) reception unit 9 of biological sample measuring instrument 1, control unit 16 reads measurement-related information using reading unit 22 (S23, NO). Specifically, the measurer holds (puts) transmission/reception area 24 (see FIG. 2) of measurement-related information supply instrument 8 over (close to) IC tag 25 incorporated in bracelet 20 (see FIG. 5) of the patient. Accordingly, the patient ID in IC tag 25 is authenticated and read by reading unit 22 serving as an RFID reader, and is stored in storage unit 19 through control unit 16 (S24).

At this time, control unit 16 may generate electronic sound, such as "beep", from buzzer 18 as notification of the completion of patient ID recognition. With this electronic sound, the measurer can recognize that the patient ID is read by reading unit 22. After the patient ID is read, control unit 16 returns to the processing of Step S21.

After the patient ID is read, the measurer performs an operation to read the biological sample sensor ID of sensor bottle 21.

Specifically, similarly to the reading operation of the patient ID, if the measurer presses power switch 15 of measurement-related information supply instrument 8, power of battery 17 is supplied to measurement-related information supply instrument 8 (S21), and control unit 16 of measurement-related information supply instrument 8 enters the reading mode (S22). Next, control unit 16 confirms the presence/absence of a communication request to be sent from biological sample measuring instrument 1 in Step S3 (see FIG. 7) using reading unit 22 (S23).

When there is no communication request from biological sample measuring instrument 1 (S23, NO), the measurer holds (puts) transmission/reception area 24 (see FIG. 2) of measurement-related information supply instrument 8 over (close to) IC tag 26 incorporated in sensor bottle 21 (see FIG. 6). Then, the biological sample sensor ID in IC tag 26 is authenticated and read by reading unit 22, and is stored in storage unit 19 through control unit 16 (S24).

At this time, control unit 16 may generate electronic sound different from at the time of the completion of the reading of the patient ID, such as "double beep", as notification of the completion of biological sample sensor ID recognition from buzzer 18. With this electronic sound, the measurer can recognize that the biological sample sensor ID is read by reading unit 22. After the biological sample sensor ID is read, control unit 16 returns to the processing of Step S21.

Next, the measurer performs an operation to transmit the read measurement-related information to biological sample measuring instrument 1.

Specifically, the measurer presses power switch 15 of measurement-related information supply instrument 8. Accordingly, as described above, power is supplied to measurement-related information supply instrument 8 (S21), control unit 16 of measurement-related information supply instrument 8 enters the reading mode (S22) and control unit 16 confirms the presence/absence of a communication request to be sent from biological sample measuring instrument 1 (S23).

In this state, the measurer holds (puts) transmission/reception area 24 of measurement-related information supply instrument 8 over (close to) reception unit 9 provided on the top surface of main body case 2 of biological sample measuring instrument 1 (see FIG. 1). Then, control unit 16 receives a communication request from biological sample measuring instrument 1 through reading unit 22 (S23, YES), and control unit 16 enters a reply mode. At this time, control unit 16 gives reply notification to reception unit 9 of biological sample measuring instrument 1 through transmission unit 23 (S25).

Next, control unit 16 transmits the patient ID and the biological sample sensor ID as measurement-related information read into measurement-related information supply instrument 8 and stored in storage unit 19, and the measurer ID stored in advance in storage unit 19 to reception unit 9 of biological sample measuring instrument 1 using transmission unit 23 (S26).

Control unit 16 erases the measurement-related information read into measurement-related information supply instrument 8 and stored in storage unit 19, specifically, the patient ID and the biological sample sensor ID (S27), and ends reading of a series of measurement-related information (S28).

Returning to FIG. 7, the continuation of the operation of biological sample measuring instrument 1 will be described.

In Step S4, if the reply notification is received from measurement-related information supply instrument 8 through reception unit 9 (S25) (S4, YES), subsequently, biological sample measuring instrument 1 receives the measurement-related information from measurement-related information supply instrument 8. Specifically, the patient ID and the biological sample sensor ID as the measurement-related information, and the measurer ID are received (S5).

Meanwhile, in Step S4, if the reply notification is not received from measurement-related information supply instrument 8 through reception unit 9 (S4, NO), biological sample measuring instrument 1 returns to Step S3.

Control unit 12 of biological sample measuring instrument 1 which receives the measurement-related information from measurement-related information supply instrument 8 confirms whether or not all kinds of information are collected (S6). When either of the measurer ID, the patient ID, and the biological sample sensor ID is lacking, for example, when the patient ID is lacking (S6, NO), as shown in FIG. 9, control unit 12 of biological sample measuring instrument 1 performs display regarding lacking in information, such as "NO PATIENT ID." "PLEASE READ ALL IDs AGAIN.", on display unit 6 (S7).

Figure 9:
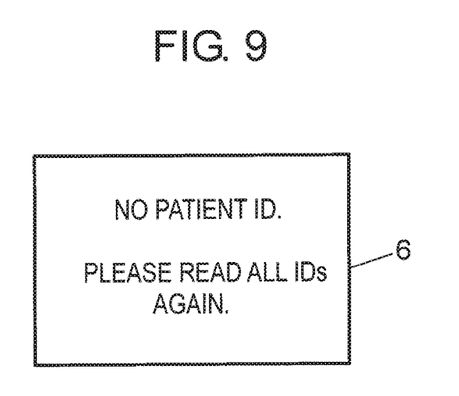
FIG. 9 is a diagram showing display details of a biological sample measuring instrument in an embodiment of the invention.

FIG. 9 is a diagram showing display details of biological sample measuring instrument 1 in the embodiment of the invention.

The measurer who views the display shown in FIG. 9 reads the patient ID, the biological sample sensor ID, and the like using measurement-related information supply instrument 8 again, and holds transmission/reception area 24 of measurement-related information supply instrument 8 over reception unit 9 on the top surface of main body case 2 of biological sample measuring instrument 1 again to transmit information to biological sample measuring instrument 1 (S21 to S27). Control unit 12 of biological sample measuring instrument 1 returns to Step S3 and repeats the procedure of Steps S3 to S6 to receive the information from measurement-related information supply instrument 8.

In Step S6, when all kinds of information are collected (S6, YES), control unit 12 stores the measurement-related information in storage unit 13, and control unit 12 enters a measurement mode (S8).

Thereafter, the measurer mounts connection terminal 4 of blood glucose level sensor 3 in sensor mounting portion 5 of biological sample measuring instrument 1, and spots blood in spotting portion 10 at the leading end of blood glucose level sensor 3 (S9). Then, the blood glucose level of blood is measured by measurement unit 11 (see FIG. 3) and stored in storage unit 13 (S10). At this time, the blood glucose level may be displayed on display unit 6.

The measurer repeats the procedure of Steps S3 to S10 by the number of patients. When it is determined that all measurements end, the measurer returns biological sample measuring instrument 1 onto the cradle (not shown). At this time, in control unit 12 of biological sample measuring instrument 1, connection terminal 14 for providing the measurement-related information and the blood glucose level stored in storage unit 13 to an external device (for example, the cradle) is electrically connected to a connection terminal (not shown) of the cradle.

Then, control unit 12 of biological sample measuring instrument 1 determines that the measurements end (S11, YES), and sends the measurement-related information and the blood glucose level of storage unit 13 to the external device (for example, the cradle) through connection terminal 14 (S12). At the hospital, it becomes possible to manage the measurement-related information in association with the blood glucose level.

Meanwhile, as described above, when the measurer does not return biological sample measuring instrument 1 onto the cradle, control unit 12 returns to Step S3 (S11, NO).

As described above, in this embodiment, biological sample measuring instrument 1 reads measurement-related information from measurement-related information supply instrument 8 having a thin plate square card shape by electric waves. Accordingly, measurement-related information supply instrument 8 is held over IC tag 25 of bracelet 20 or IC tag 26 of sensor bottle 21, and thus it is possible to read the measurement-related information, such as the patient ID and the biological sample sensor ID, by electric waves. The measurer ID of measurement-related information supply instrument 8 can be added to the read measurement-related information and transmitted to biological sample measuring instrument 1 by electric waves.

Accordingly, unlike the related art, it is not necessary for the measurer to read various kinds of measurement-related information with the heavy main body of biological sample measuring instrument 1 including measurement unit 11, display unit 6, and battery 27, and the like. As a result, even in a hard hospital service, it is possible to reduce the burden on the measurer.

In this embodiment, since measurement-related information supply instrument 8 is held over IC tag 25 of bracelet 20 and IC tag 26 of sensor bottle 21 to read the patient ID or the biological sample sensor ID, unlike a reading unit (for example, a barcode reader) of the related art, it is possible to read necessary measurement-related information without paying attention to the direction of reading. There is no case where reading light of the barcode reader is incident on the eyes of the patient when using the barcode reader. From this point, it is also possible to reduce the burden on the measurer.

In measurement-related information supply instrument 8 of this embodiment, power switch 15 is provided near the outer edge of the surface of plate-shaped measurement-related information supply instrument 8, specifically, in the lower left portion (the lower left side of FIG. 2) on the surface of square measurement-related information supply instrument 8. It is preferable that power switch 15 is provided at a location at which there is no interference with transmission/reception area 24 provided in the central portion of the surface of measurement-related information supply instrument 8.

Accordingly, for power switch 15 provided near the outer edge of plate-shaped measurement-related information supply instrument 8, the measurer sandwiches the front and rear surfaces of measurement-related information supply instrument 8 between his/her thumb and forefinger to press power switch 15. In this case, since measurement-related information supply instrument 8 is retained in a state where transmission/reception area 24 in the central portion of the surface thereof is opened widely, the reading operation of the patient ID, the biological sample sensor ID, or the like is facilitated.

In this embodiment, a pressure-sensitive switch is used as power switch 15. For this reason, even when measurement-related information supply instrument 8 is put in a transparent resin case so as to be put on the chest of the measurer, the measurer presses power switch 15 with his/her finger from above the resin case to turn on the switch.

In this embodiment, a configuration in which power of battery 17 is supplied to control unit 16 of measurement-related information supply instrument 8 only when power switch 15 is in the pressure-sensitive state (on state) is made. For this reason, if the reading operation of the measurement-related information (the patient ID and the biological sample sensor ID) ends and the measurer separates his/her finger from power switch 15, power supply to control unit 16 of measurement-related information supply instrument 8 is immediately shut off, and the measurement-related information is not read any more.

That is, in this state (the state where the finger is separated from power switch 15), even if a sensor bottle or the like other than sensor bottle 21 to be measured becomes close to transmission/reception area 24 in the central portion of the surface of measurement-related information supply instrument 8, there is no case where the biological sample sensor ID of the sensor bottle or the like close to transmission/reception area 24 is erroneously read. From this point, it is also possible to reduce the burden on the measurer.

In this embodiment, a configuration in which power of battery 17 is supplied to control unit 16 of measurement-related information supply instrument 8 only when power switch 15 is in a pressure-sensitive state is made. However, the invention is not limited to this example. For example, a configuration in which, when power switch 15 enters the pressure-sensitive state, control unit 16 of measurement-related information supply instrument 8 measures a predetermined time (for example, 10 seconds) using a timer (not shown), and then power supply from battery 17 to control unit 16 is shut off may be made.

With this configuration, the measurer can end the reading operation of the measurement-related information (the patient ID and the biological sample sensor ID) within a predetermined time (for example, 10 seconds). Since power supply to control unit 16 is shut off after the predetermined time, there is little possibility that the measurement-related information is erroneously read.

Measurement-related information supply instrument 8 in this embodiment is configured to erase the measurement-related information (the patient ID and the biological sample sensor ID) read by RFID and stored in storage unit 19 from storage unit 19 after transmitting to reading unit 22 of biological sample measuring instrument 1 by electric waves. For this reason, when reading the next measurement-related information, since the previous measurement-related information is completely erased from storage unit 19, there is no case where the next measurement-related information and the previous measurement-related information are confused with each other.

When measurement-related information supply instrument 8 transmits the measurement-related information (the patient ID and the biological sample sensor ID) to biological sample measuring instrument 1, control unit 16 of measurement-related information supply instrument 8 determines the pressure-sensitive state of power switch 15 after transmission. After it is confirmed that power switch 15 is not in the pressure-sensitive state, control unit 16 shuts off power supply from battery 17.

As a result, it is possible to transmit correct measurement-related information to biological sample measuring instrument 1 and to reduce the burden on the measurer.

As described above, in this embodiment, reading unit 22 of the measurement-related information is arranged in measurement-related information supply instrument 8 provided separately from biological sample measuring instrument 1. Therefore, the measurer can read the measurement-related information, such as the patient ID and the biological sample sensor ID, using measurement-related information supply instrument 8 and can transmit the read measurement-related information to biological sample measuring instrument 1 with the identification information of measurement-related information supply instrument 8.

Therefore, it is not necessary for the measurer to read various kinds of measurement-related information with a heavy biological sample measuring instrument main body including a barcode scanner, a display unit, and the like, and as a result, it is possible to reduce the burden on the measurer.

INDUSTRIAL APPLICABILITY

As described above, according to the invention, it is possible to obtain a particular effect that it is possible to reduce the burden on the measurer. Therefore, the invention is useful as a biological sample measurement device including a biological sample measuring instrument and a measurement-related information supply instrument which supplies measurement-related information to the biological sample measuring instrument, for example, a biological sample measurement device which measures biological information, such as a blood glucose level, from blood, or the like.

REFERENCE MARKS IN THE DRAWINGS

1: biological sample measuring instrument
2: main body case
3: blood glucose level sensor
4: connection terminal
5: sensor mounting portion
6: display unit
7, 15: power switch
8: measurement-related information supply instrument
9: reception unit
10: spotting portion
11: measurement unit
12, 16: control unit
13, 19: storage unit
14: connection terminal
17, 27: battery
18: buzzer
20: bracelet
21: sensor bottle
22: reading unit
23: transmission unit
24: transmission/reception area
25, 26: IC tag

The invention claimed is:

1. A biological sample measurement device comprising:
a biological sample measuring instrument;
a cradle configured to be electrically connected to the biological sample measuring instrument; and
a measurement-related information supply instrument configured to supply a plurality of measurement-related information pieces to the biological sample measuring instrument,
wherein the measurement-related information supply instrument has
a reading unit configured to read the plurality of measurement-related information pieces from a plurality of IC tags by proximity communication through an electric wave, and
a transmission unit configured to add measurer identification information identifying a measurer to the plurality of measurement-related information pieces read from the plurality of IC tags and transmit the plurality of measurement-related information pieces to which the measurer identification information is added, the biological sample measuring instrument having a display unit, a main body case having a mounting portion for a separately housed biological sample sensor, a measurement unit connected to the mounting portion inside the main body case, a control unit connected to the measurement unit, and a reception unit configured to receive the plurality of measurement-related information pieces to which the measurer identification information is added, and the control unit configured to transmit the plurality of measurement-related information pieces to which the measurer identification information is added and a measured value measured by the measurement unit to the cradle.

2. The biological sample measurement device according to claim 1, wherein the biological sample measuring instrument has a connection terminal for transmitting the plurality of measurement-related information pieces to which the measurer identification information is added and the measured value to the cradle; and wherein the connection terminal is connected to the control unit.

3. The biological sample measurement device according to claim 1, wherein the reception unit is provided on a surface of the main body case of the biological sample measuring instrument.

4. The biological sample measurement device according to claim 1, each of the plurality of measurement-related information pieces to which the measurer identification information is added has a measurer ID, a patient ID, and a biological sample sensor ID.

5. The biological sample measurement device according to claim 1, wherein the control unit stores the plurality of measurement-related information pieces to which the measurer identification information is added in a storage unit and enters a measurement mode.

6. The biological sample measurement device according to claim 1, wherein the display unit performs a display regarding a lack of information when either of a measurer ID, a patient ID, and/or a biological sensor ID is lacking in one of the plurality of measurement-related information pieces to which the measurer identification information is added.

* * * * *